(12) United States Patent
Lenz

(10) Patent No.: US 7,179,286 B2
(45) Date of Patent: Feb. 20, 2007

(54) STENT WITH STEPPED CONNECTORS

(75) Inventor: Jason T. Lenz, Maplewood, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/371,804

(22) Filed: Feb. 21, 2003

(65) Prior Publication Data

US 2004/0167615 A1 Aug. 26, 2004

(51) Int. Cl.
*A61F 2/06* (2006.01)
(52) U.S. Cl. ..................... 623/1.15; 623/23.7
(58) Field of Classification Search ............. 623/1, 623/11.11, 12, 23.71; 606/191–200
See application file for complete search history.

(56) References Cited

U.S. PATENT DOCUMENTS

| | | | |
|---|---|---|---|
| 4,733,665 A | 3/1988 | Palmaz | 128/343 |
| 5,091,205 A | 2/1992 | Fan | 427/2 |
| 5,102,417 A | 4/1992 | Palmaz | 606/195 |
| 5,314,472 A | 5/1994 | Fontaine | 623/12 |
| 5,449,373 A | 9/1995 | Pinchasik et al. | 606/198 |
| 5,507,767 A | 4/1996 | Maeda et al. | 606/198 |
| 5,591,227 A | 1/1997 | Dinh et al. | 623/1 |
| 5,593,442 A | 1/1997 | Klein | 623/12 |
| 5,599,352 A | 2/1997 | Dinh et al. | 623/1 |
| 5,613,981 A | 3/1997 | Boyle et al. | 606/198 |
| 5,624,411 A | 4/1997 | Tuch | 604/265 |
| 5,653,727 A | 8/1997 | Wiktor | 606/195 |
| 5,679,400 A | 10/1997 | Tuch | 427/2.14 |
| 5,733,303 A | 3/1998 | Israel et al. | 606/198 |
| 5,735,871 A | 4/1998 | Sgro | 606/198 |
| 5,755,770 A | 5/1998 | Ravenscroft | 623/1 |
| 5,759,192 A | 6/1998 | Saunders | 606/194 |
| 5,776,161 A | 7/1998 | Globerman | 606/194 |
| 5,776,183 A | 7/1998 | Kanesaka et al. | 623/1 |
| 5,807,404 A | 9/1998 | Richter | 623/1 |
| 5,810,872 A | 9/1998 | Kanesaka et al. | 606/198 |
| 5,824,043 A | 10/1998 | Cottone, Jr. | 623/1 |
| 5,824,046 A | 10/1998 | Smith et al. | 623/1 |
| 5,824,048 A | 10/1998 | Tuch | 623/1 |
| 5,895,406 A | 4/1999 | Gray et al. | 606/198 |
| 5,897,588 A | 4/1999 | Hull et al. | 623/1 |
| 5,900,246 A | 5/1999 | Lambert | 424/429 |
| 5,902,332 A | 5/1999 | Schatz | 623/1 |
| 5,911,754 A | 6/1999 | Kanesaka et al. | 623/1 |
| 5,922,021 A | 7/1999 | Jang | 623/1 |

(Continued)

FOREIGN PATENT DOCUMENTS

EP  1 245 203 A2  10/2002

(Continued)

*Primary Examiner*—David J. Isabella
(74) *Attorney, Agent, or Firm*—Vidas, Arrett & Steinkraus, P.A.

(57) ABSTRACT

A stent comprises a plurality of serpentine circumferential bands and a plurality of connector columns. Each connector column is located between two adjacent serpentine circumferential bands and comprises a plurality connector struts. Each connector strut is connected at one end to one serpentine circumferential band and at another end to another serpentine circumferential band. Each connector strut has step sections and at least one riser. Each step section extends substantially in a circumferential direction and each riser extends in a substantially longitudinal direction. The steps in a connector are connected to one another via a riser.

28 Claims, 2 Drawing Sheets

U.S. PATENT DOCUMENTS

| | | | |
|---|---|---|---|
| 5,938,682 A | 8/1999 | Hojeibane et al. | 606/198 |
| 5,948,016 A | 9/1999 | Jang | 623/1 |
| 5,951,586 A | 9/1999 | Berg et al. | 606/198 |
| 5,954,743 A | 9/1999 | Jang | 606/198 |
| 5,980,553 A | 11/1999 | Gray et al. | 606/198 |
| 5,984,016 A | 11/1999 | Samuelsson | 169/62 |
| 6,039,756 A * | 3/2000 | Jang | 623/1.15 |
| 6,053,940 A | 4/2000 | Wijay | 623/1 |
| 6,120,522 A | 9/2000 | Vrba et al. | 606/190 |
| 6,123,721 A | 9/2000 | Jang | 623/1 |
| 6,133,627 A | 10/2000 | Khandros et al. | 257/692 |
| 6,152,957 A | 11/2000 | Jang | 623/1.37 |
| 6,190,403 B1 | 2/2001 | Fischell et al. | 623/1 |
| 6,193,744 B1 | 2/2001 | Ehr et al. | 623/1 |
| 6,193,747 B1 | 2/2001 | von Oepen | 623/1.15 |
| 6,200,334 B1 | 3/2001 | Jang | 623/1.1 |
| 6,231,598 B1 | 5/2001 | Berry et al. | 623/1.15 |
| 6,235,053 B1 | 5/2001 | Jang | 623/1.15 |
| 6,241,760 B1 | 6/2001 | Jang | 623/1.12 |
| 6,331,189 B1 | 12/2001 | Wolinsky et al. | 623/1.15 |
| 6,355,059 B1 | 3/2002 | Richter et al. | 623/1.17 |
| 6,379,379 B1 | 4/2002 | Wang | 623/1.15 |
| 6,379,382 B1 | 4/2002 | Yang | 623/1.42 |
| 6,387,122 B1 | 5/2002 | Cragg | 623/1.16 |
| 6,409,761 B1 | 6/2002 | Jang | 623/6.12 |
| 6,416,538 B1 | 7/2002 | Ley et al. | 623/1.15 |
| 6,423,090 B1 | 7/2002 | Hancock | 623/1.15 |
| 6,432,133 B1 | 8/2002 | Lau et al. | 623/1.15 |
| 6,776,793 B2 * | 8/2004 | Brown et al. | 623/1.15 |
| 2001/0020183 A1 | 9/2001 | Jang | 623/1.15 |
| 2002/0120327 A1 | 8/2002 | Cox et al. | 623/1.16 |
| 2003/0033007 A1 | 2/2003 | Sirhan et al. | 623/1.42 |

FOREIGN PATENT DOCUMENTS

| | | |
|---|---|---|
| WO | 96/03092 | 2/1996 |
| WO | 97/32543 | 9/1997 |
| WO | 98/40035 | 9/1998 |
| WO | 99/01088 | 1/1999 |
| WO | 99/15107 | 4/1999 |

* cited by examiner

STENT WITH STEPPED CONNECTORS

BACKGROUND OF THE INVENTION

The use of stents in bodily lumen is well known. A stent is typically delivered in an unexpanded state to a desired location in a bodily lumen via a stent delivery device such as a catheter. Once the stent is at the desired bodily location, it is either expanded with a balloon or other suitable device or allowed to expand by, for example, withdrawing a restraining sheath. Typically, the stent is delivered bare to the body. During the past several years, however, there has been a great deal of interest in drug-coated stents. Specifically, a number of drug-coated stents have been developed which allow for time-release of a drug. These stents are believed to offer the possibility of reduced restenosis. The presence of drug-coatings on stents, however, presents new challenges in the area of stent design. Conventional bare stent designs may prove difficult to coat uniformly because of the proximity of different structural features.

There is a need for flexible stents that are designed to be coated with drugs.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

BRIEF SUMMARY OF THE INVENTION

In one embodiment, the invention is directed to a stent comprising a plurality of serpentine circumferential bands, and a plurality of connector columns. Each connector column is located between two adjacent circumferential bands and comprises one or more connector struts. Each connector strut is connected at one end to one serpentine circumferential band and at another end to another serpentine circumferential band. Each connector strut further comprises step and riser elements. Desirably each connector strut comprises only two step sections and no more than three riser elements.

In another embodiment, the invention is directed to a stent comprising a plurality of serpentine circumferential bands comprising alternating peaks and troughs, and a plurality of connector columns. Each connector column is located between two adjacent circumferential bands and includes a plurality connector struts. Typical connector struts within a connector column are distributed such that between each peak on one serpentine circumferential band and a facing trough on an adjacent serpentine circumferential band, there are at least three different connector struts.

Additional details and/or embodiments of the invention are discussed below.

BRIEF DESCRIPTION OF DRAWINGS

FIG. 1a shows a flat pattern of an inventive stent.

FIG. 1b shows an expanded view of a connector strut of FIG. 1a.

DETAILED DESCRIPTION OF THE INVENTION

Figure 1:
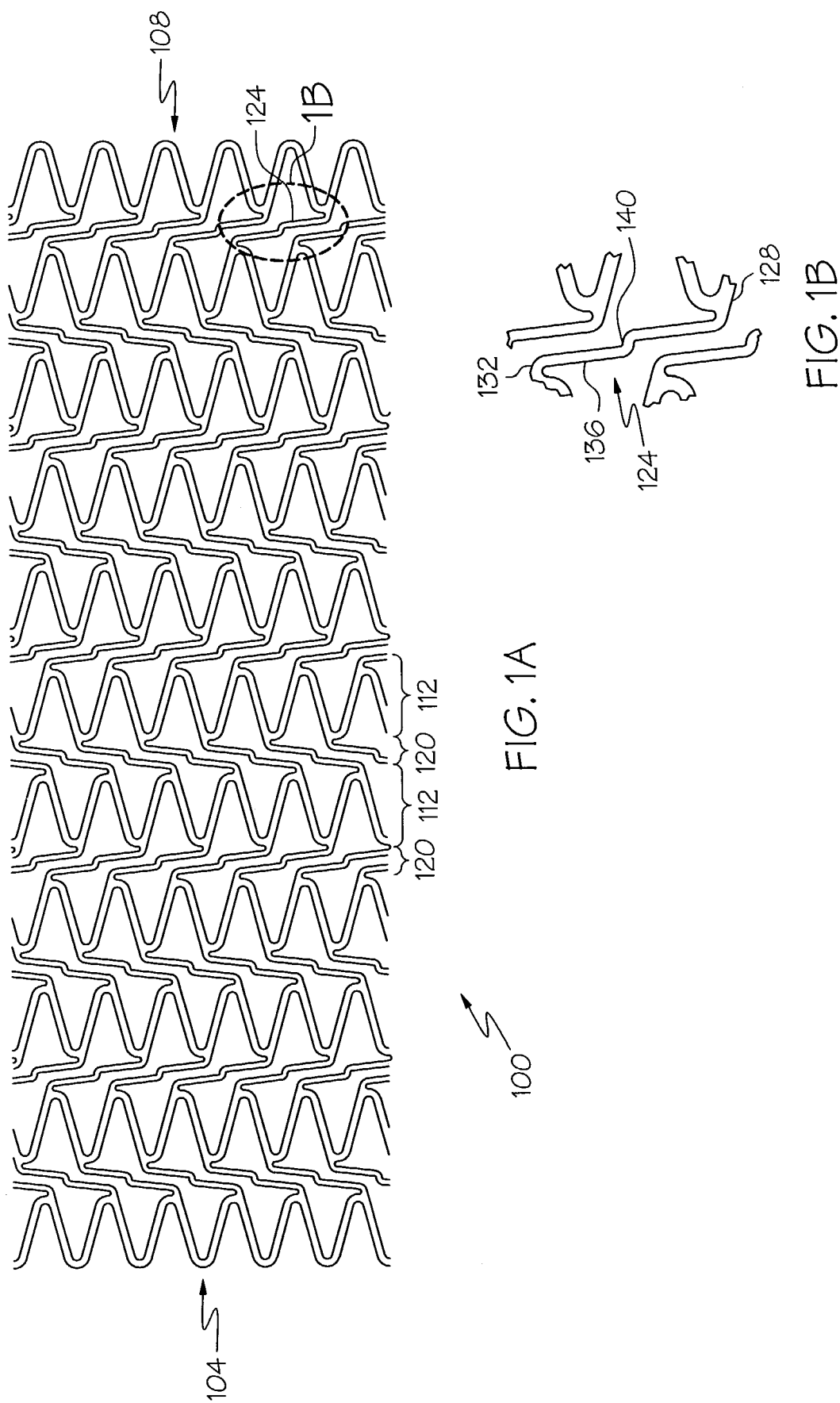

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In one embodiment, the invention is directed to a stent such as that shown generally at 100 in FIG. 1a, having a first free end 104 and a second free end 108, comprising a plurality of serpentine circumferential bands 112, and a plurality of connector columns 120. Each serpentine circumferential band 112 may form a plurality of alternating peaks and troughs. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band.

Each connector strut 124 may further be comprised of one or more step sections 136 and one or more risers 140. The step sections 136 may be perpendicular to the longitudinal axis of the stent 100, and the risers 140 may be parallel to the longitudinal axis of the stent 100. Thus, the connector struts 124 may be characterized as forming stair-steps. The connector struts 124 may further be characterized as being substantially straight with a jog therein.

Optionally, the step sections 136 may be slanted or arranged at a slight to moderate angle to an axis perpendicular to the longitudinal axis of the stent 100. Likewise, the risers 140 may be arranged at a slight to moderate angle to the longitudinal axis of the stent 100. Slanted step sections 136 and risers 140 are depicted in FIGS. 1a–3.

Figure 2:
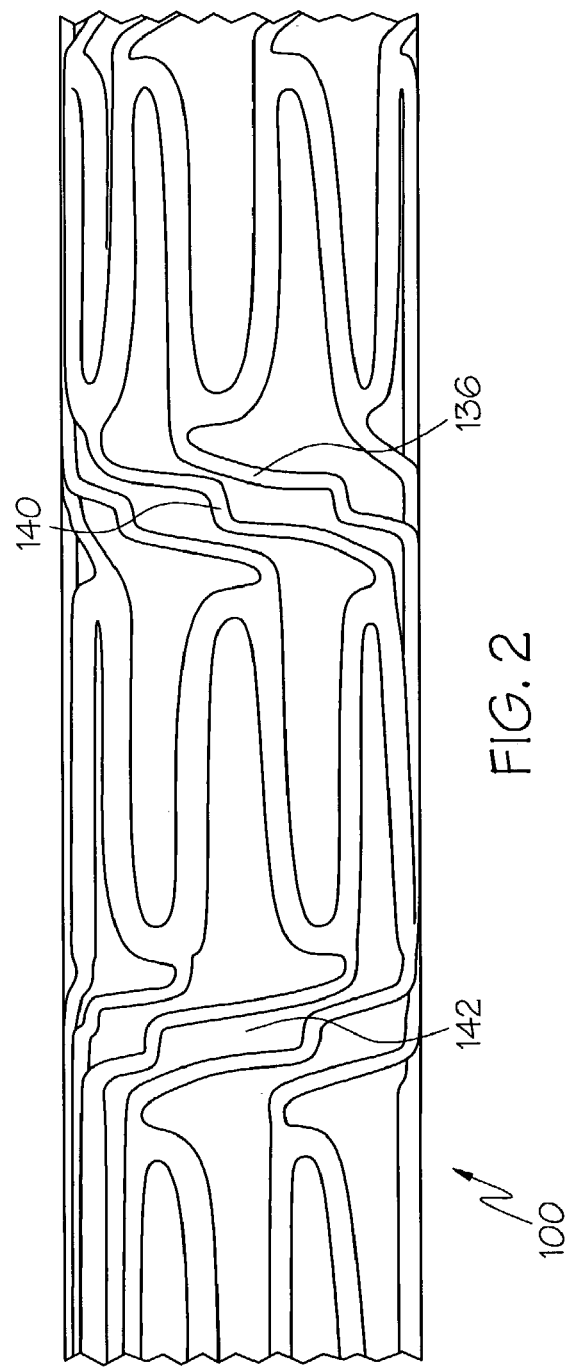
FIG. 2 shows the stent of FIG. 1 in a crimped state, such as crimped onto a balloon.
Figure 3:
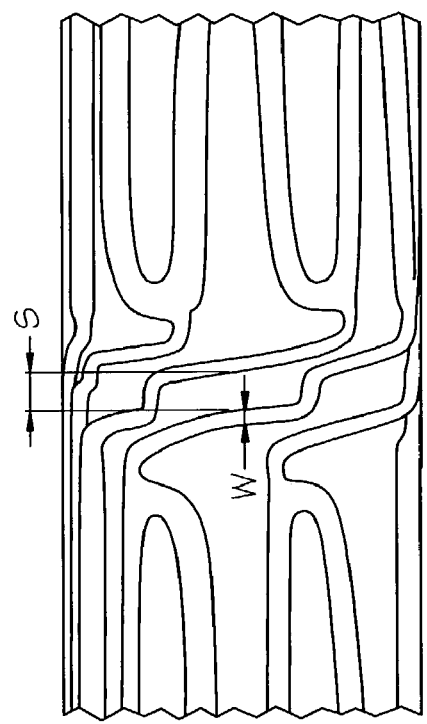
FIG. 3 shows the stent of FIG. 1 in a crimped state.

As best shown in FIGS. 2 and 3, which depict an embodiment of the stent 100 in a crimped, unexpanded state, such as about an expansion balloon or catheter, the risers 140 may act to space the step sections 136 laterally with respect to each other. In the embodiment shown, there are three different connector struts 124 located between each peak on one serpentine circumferential band 112 and a facing trough on an adjacent serpentine circumferential band 112. Thus, each connector strut 124 contacts two circumferentially adjacent connector struts 124. Further, adjacent connector struts 124 define a substantially parallelogram shaped space 142 bounded by two risers 140 and two step sections 136. This provides the stent 100 with added flexibility in bending about the length of the stent 100 while still retaining structural rigidity against compressive axial forces.

Lateral spacing S of the step sections 136 is directly affected by the length of the risers 140 and the angle formed between the risers 140 and the step sections 136. While lateral spacing of the step sections 136 may be set to any practical configuration, the embodiment depicted in FIGS. 2 and 3 utilizes a lateral spacing S in the unexpanded state of approximately four times the width W of the step sections 136.

In some embodiments, step sections which are connected to one another via a riser may be separated from one another by a spacing of less than four times the width of a step section.

A further benefit of the risers 140, and the subsequent lateral spacing of the step sections 136, may be realized when the present stent 100 is used with a coating, such as a drug coating. Because adjacent step sections 136 are not in lateral contact with each other for a substantial portion of their length, coatings may be applied more uniformly to the entire surface area of the stent 100. The lateral spacing helps to assure that the sides of the step sections 136 are properly coated.

The lateral spacing also helps to prevent a coating from forming a thick film extending across multiple adjacent step sections 136 over substantial lengths of the step sections 136. This is beneficial because a thick film extending across multiple adjacent step sections 136 can cause the step sections 136 to stick together upon expansion, interfering with proper deployment and functionality after placement.

Although FIGS. 1*a*–3 depict an embodiment of the stent 100 having a plurality of similar serpentine circumferential bands 112, various embodiments may include different serpentine forms, such as bands of different length, bands of different widths, bands having varying numbers of peaks and troughs, and the like.

Similarly, the stent 100 embodiment shown in FIGS. 1*a*–3 includes connector columns 120 wherein the connector struts 124 reverse orientation from column to column. Additional embodiments may include configurations wherein all connector struts 124 are similarly aligned. Further, various other shapes of connecting struts 124 may be utilized in accordance with the present inventive stent 100.

Suitable methods for manufacturing the inventive stents include laser cutting, chemical etching or stamping of a tube. The inventive stents may also be manufactured by laser cutting, chemically etching, stamping a flat sheet, rolling the sheet and welding the sheet, by electrode discharge machining, or by molding the stent with the desired design. The stent may also be manufactured by assembling a plurality of serpentine circumferential bands and welding or adhesively joining them to one another via connectors.

Any suitable stent material may be used in the manufacture of the inventive stents disclosed herein. Examples of such materials include polymeric materials, metals, ceramics and composites. Suitable polymeric materials include thermotropic liquid crystal polymers (LCP's). Where the stent is made of metal, the metal may be stainless steel, cobalt chrome alloys such as elgiloy, tantalum or other plastically deformable metals. Other suitable metals include shape-memory metals such as nickel titanium alloys generically known as "nitinol," platinum/tungsten alloys and titanium alloys. The invention also contemplates the use of more than one material in the inventive stents. For example, the first serpentine bands and the second serpentine bands may be made of different materials. Optionally, the connectors may be made of a different material than the first and/or second serpentine bands.

The inventive stents disclosed herein may be balloon-expandable, self-expanding or a hybrid of the two.

In the case of balloon-expandable stents, a balloon catheter may be used to deliver the stent to a desired bodily location. The balloon is then expanded, causing the stent to expand. The balloon may then be deflated and the catheter withdrawn. In the case of a self-expanding stent, the stent may be delivered on a catheter suited for delivery of self-expanding stents. Typically, such catheters include will include a retention sheath to maintain the stent in position until it is to be deployed. At the time of deployment, the sheath is withdrawn and the stent allowed to expand.

The invention is also directed to a stent-delivery catheter and any of the inventive stents disclosed herein. Details of stent-delivery catheters may be found in U.S. Pat. No. 6,120,522 and U.S. Pat. No. 6,506,201.

The inventive stents disclosed herein may include suitable radiopaque coatings. For example, the stents may be coated with gold or other noble metals or sputtered with tantalum or other metals. The stents may also be made directly from a radiopaque material to obviate the need for a radiopaque coating or may be made of a material having a radiopaque inner core. Other radiopaque metals which may be used include platinum, platinum-tungsten, palladium, platinum-iridium, rhodium, tantalum, or alloys or composites of these metals.

The inventive stents may also be provided with various bio-compatible coatings to enhance various properties of the stent. For example, the inventive stents may be provided with lubricious coatings. The inventive stents may also be provided with drug-containing coatings which release drugs over time.

The inventive stents may also be provided with a sugar or more generally a carbohydrate and/or a gelatin to maintain the stent on a balloon during delivery of the stent to a desired bodily location. Other suitable compounds for treating the stent include biodegradable polymers and polymers which are dissolvable in bodily fluids. Portions of the interior and/or exterior of the stent may be coated or impregnated with the compound. Mechanical retention devices may also be used to maintain the stent on the balloon during delivery.

The inventive medical devices may also be provided with various bio-compatible coatings to enhance various properties of the inventive medical devices. For example, the inventive medical devices may be provided with lubricious coatings or other polymeric coatings. An example of a suitable polymeric coating is PTFE.

The inventive stents may include one or more coatings which comprise one or more therapeutic agents, cellular materials, polymeric agents, and the like. Coatings may be applied to the stent in numerous ways, including spray coatings, dip coatings, or any other method that is known in the art.

The therapeutic agent may be non-genetic or genetic. Suitable non-genetic therapeutic agents include anti-thrombogenic agents such as heparin, heparin derivatives, urokinase, and PPack (dextrophenylalanine proline arginine chloromethylketone), anti-proliferative agents such as enoxaprin, angiopeptin, or monoclonal antibodies capable of blocking smooth muscle cell proliferation, hirudin, and acetylsalicylic acid, anti-inflammatory agents such as dexamethasone, prednisolone, corticosterone, budesonide, estrogen, sulfasalazine, and mesalamine, antineoplastic/antiproliferative/anti-miotic agents such as paclitaxel, 5-fluorouracil, cisplatin, vinblastine, vincristine, epothilones, endostatin, angiostatin and thymidine kinase inhibitors, anesthetic agents such as lidocaine, bupivacaine, and ropivacaine, anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides, vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol-lowering agents; vasodilating agents; and agents which interfere with endogenous vasoactive mechanisms.

Suitable genetic materials include anti-sense DNA and RNA, DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation, the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7 are particularly desirable. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Suitable cellular materials include cells of human origin (autologous or allogeneic) or from an animal source (xenogeneic), genetically engineered if desired to deliver proteins of interest at the transplant site. The delivery media can be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (BAY-HDROL®, etc.), fibrin, collagen and derivatives thereof, polysaccharides such as celluloses, starches, dextrans, alginates and derivatives, hyaluronic acid, squalene emulsions. Desirably, polyacrylic acid, available as HYDROPLUS® (Boston Scientific Corporation, Natick, Mass.), and described in U.S. Pat. No. 5,091,205, the disclosure of which is hereby incorporated herein by reference, may be used. Also desirably, the polymer may be a copolymer of polylactic acid and polycaprolactone. Other materials include selected medical-grade biodegradable materials such as PGA-TMC, Tyrosine-Derived Polycarbonates and arylates, polycaprolactone co butyl acrylate and other co polymers, Poly-L-lactic acid blends with DL-Lactic Acid, Poly(lactic acid-co-glycolic acid), polycaprolactone co PLA, polycaprolactone co butyl acrylate and other copolymers, Tyrosine-Derived Polycarbonates and arylate, poly amino acid, polyphosphazenes, polyiminocarbonates, polydimethyltrimethylcarbonates, biodegradable CA/PO$_4$'s, cyanoacrylate, 50/50 DLPLG, polydioxanone, polypropylene fumarate, or polydepsipeptides.

Other suitable coatings include macromolecules such as chitosan and Hydroxylpropylmethylcellulose. Surface erodible materials may also be used. Coatings may also comprise maleic anhydride copolymers, zinc-calcium phosphate and amorphous polyanhydrides.

The inventive stents may also be used as the framework for a graft. Suitable coverings include nylon, collagen, PTFE and expanded PTFE, polyethylene terephthalate and KEVLAR, or any of the materials disclosed in U.S. Pat. No. 5,824,046 and U.S. Pat. No. 5,755,770. More generally, any known graft material may be used including synthetic polymers such as polyethylene, polypropylene, polyurethane, polyglycolic acid, polyesters, polyamides, their mixtures, blends, copolymers, mixtures, blends and copolymers.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

In addition to the specific embodiments claimed below, the invention is also directed to other embodiments having any other possible combination of the dependent features claimed below. As such, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 1 or claim 2; claim 11 may be taken as alternatively dependent on any of claims 9–10; claim 12 may be taken as alternatively dependent on any of claims 9–11 etc.).

Those familiar with the art may recognize other equivalents to the specific embodiments described herein which equivalents are also intended to be encompassed by the claims attached hereto.

The invention claimed is:

1. A stent comprising:
   a plurality of serpentine circumferential bands, at least one serpentine circumferential band having alternating peaks and troughs connected by straight elements, a first straight element being non-parallel to a second straight element when the stent is unexpanded, and
   a plurality of connector columns, each connector column located between two adjacent serpentine circumferential bands, each connector column comprising a plurality of connector struts, each connector strut connected at one end to one serpentine circumferential band and at another end to another serpentine circumferential band, each connector strut having only two step sections and at least one and no more than three risers, each step section extending substantially in a circumferential direction, each riser extending in a substantially longitudinal direction, the step sections in a connector strut connected to one another via a riser, each connector strut having a greater length in the circumferential direction than in the longitudinal direction.

2. The stent of claim 1 wherein step sections which are connected to one another via a riser are separated from one another by a spacing of less than four times the width of the step section.

3. The stent of claim 1 further comprising a coating.

4. The stent of claim 2 further comprising a coating.

5. The stent of claim 3 wherein the coating comprises a drug.

6. The stent of claim 4 wherein the coating comprises a drug.

7. The stent of claim 1 wherein the step sections are slanted with respect to an axis perpendicular to the longitudinal axis of the stent.

8. The stent of claim 1 wherein the risers are slanted with respect to the longitudinal axis of the stent.

9. A stent having a plurality of cells, the stent comprising:
a plurality of serpentine circumferential bands, each serpentine circumferential band comprising alternating peaks and troughs, and
a plurality of connector columns, a connector column located between each two adjacent serpentine circumferential bands, adjacent serpentine circumferential bands connected by a connector column, each connector column comprising a plurality of connector struts, each connector strut connected at one end to one serpentine circumferential band and at another end to another serpentine circumferential band, the connector swats in a connector column distributed such that between each peak on one serpentine circumferential band and a facing trough on an adjacent serpentine circumferential band there are at least three different connector struts,
each cell being partially bounded by a connector strut and partially bounded by a serpentine band.

10. The stent of claim 9 wherein between each peak on one serpentine circumferential band and a facing trough on an adjacent serpentine circumferential band there are only three different connector struts.

11. The stent of claim 9 wherein the connector struts are in the form of stair-steps.

12. The stent of claim 9 wherein each connector strut is substantially straight with a jog therein.

13. The stent of claim 9, each connector strut having two step sections and at least one and no more than three risers, each step section extending substantially in a circumferential direction, each riser extending in a substantially longitudinal direction, the step sections in a connector connected to one another via a riser.

14. The stent of claim 9 further comprising a coating.

15. The stern of claim 10 further comprising a coating.

16. The stent of claim 14 wherein the coating comprises a drug.

17. The stent of claim 15 wherein the coating comprises a drug.

18. The stent of claim 9 in a crimped state.

19. The stent of claim 18 wherein each connector strut contacts two circumferentially adjacent connector struts.

20. The stent of claim 18 wherein each connector strut contacts two circumferentially adjacent connector struts in locations which are between peaks of a serpentine circumferential band and facing troughs an adjacent serpentine circumferential band.

21. The stent of claim 19 wherein circumferentially adjacent connector struts which contact one another define a substantially parallelogram shaped spaced bounded by two risers and two step sections.

22. The stent of claim 21 further comprising a coating containing a drug.

23. The stent of claim 13 wherein the step sections are slanted with respect to an axis perpendicular to the longitudinal axis of the stent.

24. The stent of claim 13 wherein the risers are slanted with respect to the longitudinal axis of the stent.

25. The stent of claim 1, wherein said two step sections includes a first step section and a second step section, wherein the first step section and the second step sections slope in substantially the same direction.

26. The stent of claim 25, wherein the slope of the first step section is equal to the slope of the second step section.

27. The stent of claim 9, further comprising at least four serpentine circumferential bands and at least three connector columns.

28. A stent comprising:
a plurality of serpentine bands, each serpentine band comprising alternating peaks and troughs connected by straight struts, and
a plurality of connector columns, each connector column comprising a plurality of connector struts, each connector strut connected at a first end to a serpentine band and connected at a second end to another serpentine band;
wherein a connector column is located between each two adjacent serpentine bands, and wherein the connector struts in a connector column are distributed such that between a peak of one serpentine band and a facing trough of an adjacent serpentine band there are at least three different connector struts.

* * * * *